United States Patent
Menaker et al.

(10) Patent No.: US 6,303,931 B1
(45) Date of Patent: Oct. 16, 2001

(54) METHOD FOR DETERMINING A PROFILE QUALITY GRADE OF AN INSPECTED FEATURE

(75) Inventors: Mina Menaker, Tomer St. Reut; Andrei Veldman, Jerusalem, both of (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/193,720

(22) Filed: Nov. 17, 1998

(51) Int. Cl.⁷ .............................. G01N 23/00; G21K 7/00
(52) U.S. Cl. ............................................. 250/307; 250/310
(58) Field of Search .................................. 250/307, 310, 250/397, 492.2

(56) References Cited

U.S. PATENT DOCUMENTS

| | | | | |
|---|---|---|---|---|
| 5,199,054 | * | 3/1993 | Adams et al. | 378/21 |
| 5,404,019 | * | 4/1995 | Ohno et al. | 250/492.22 |
| 5,594,245 | * | 1/1997 | Tokodoro et al. | 250/310 |
| 5,747,202 | * | 5/1998 | Tanaka | 430/30 |
| 5,969,273 | * | 10/1999 | Archie et al. | 73/865.8 |
| 5,981,947 | * | 11/1999 | Nakasuji et al. | 250/310 |

OTHER PUBLICATIONS

"Contact Holes: A Challenge for Signal Collection Efficiency and Measurement Algorithms" Solecky et al., IBM Microelectronics SRDC East Fishkill, NY 12533, 172/ SPIE vol. 3050, pp. 172–179.

* cited by examiner

Primary Examiner—Bruce C. Anderson
(74) Attorney, Agent, or Firm—Sughrue, Mion, Zinn, Macpeak & Seas, PLLC (57) ABSTRACT

A method for determining a profile quality grade of inspected feature in a resist. The feature includes side walls. The method includes the steps of acquiring by a metrology device a signal that originates from the feature and analyzing the acquired signal, including fitting a curve from among a family of curves to the acquired signal. The curve is subjected to the following constraint: it corresponds to a signal portion that originates from part of the bottom of the feature. The method further includes the step of determining the profile quality grade of the feature depending upon characteristics of the fitted curve.

53 Claims, 6 Drawing Sheets

METHOD FOR DETERMINING A PROFILE QUALITY GRADE OF AN INSPECTED FEATURE

FIELD OF THE INVENTION

This invention relates to metrology tools for quality control of semiconductor wafers. In particular, the present invention concerns metrology tool for determining whether a contact hole (CH) in a resist or in an etched layer is open or closed.

BACKGROUND OF THE INVENTION

During the manufacturing process of semiconductor wafers, the so manufactured dies that are accommodated in the wafer undergo extensive quality control tests, including critical dimension scanning electronic microscope (CD-SEM) tests.

SEM is an electron microscope that utilizes a beam of electrons, accelerated to high energy and focused on the sample, to scan the sample surface, ejecting secondary (and possibly back-scattered) electrons that form the picture of the sample. The secondary electrons (referred to also as signal(s)) that are ejected (referred to also as originating) from the sample are acquired by the SEM. The acquisition step includes sampling and possibly other known per se operations so as to give rise to acquired SEM signals(s) (referred to also as acquired signal(s)). The latter are naturally constituted by discrete values.

The quality control tests including the CD-SEM tests are extremely important in order to assure high yield. Yield, in this connection, stands for the percentage of fault-free chips out of the entire manufacturing lot.

The continued reduction in design rules and increase in metalization layers creates a need for CD-SEM tests of high aspect ratio contact holes (CH), trenches and possibly other patterns (referred collectively as "features") for sorting out the open and closed features. The known per se utilization of resist and the pertinent quality control tests will now be briefly reviewed.

Thus, during normal manufacturing process, the resist is disposed on the substrate of the wafer and is subject to exposure and development so as to convey a pattern (that corresponds to one mask of the chip'layout) to the underlying substrate. The resist includes, as a rule, a pattern of apertures and masks. According to one out of a few known etching techniques, the apertures enable a chemical substance (normally Acid) to penetrate through the apertures and etch the underlying layer of the substrate. In contrast, the mask portion protects the underlying layer against etching. The manufacturing process of resist is error prone in particular insofar as high aspect ratio features (e.g. contact holes) are concerned. More specifically, it occasionally occurs that the specified holes, do not fully pass through the resist (i.e. they constitute closed holes) with the inevitable consequence that the underlying layer is obviously not etched (regardless of which etching technique is used). As is well known, the patterns that are conveyed to the substrate eventually realize a chip that performs electrical function(s) as defined by the design of the chip. Obviously, failing to accurately convey the pattern that corresponds to the design layout to the underlying substrate (due to inter alia faulty CH in the resist) may adversely affect the chips functional performance and may even require in some cases to discard the manufactured chips. This, of course, degrades the yield score which, from commercial stand point, is intolerable.

It is therefore highly desired to test the resist before etching in order to ascertain with high degree of confidence whether CH's, are passing through i.e. open. In the case that CH's are found to be closed, the resist is discarded and a new one is manufactured. This testing procedure has the obvious advantage (as compared to the post-etching test) in that it is not destructive for the wafer, i.e. a new layer of resist will be applied to the substrate.

In a paper by Eric Solecky and Chas Archie of IBM (Eric Solecky and Chas Archie, "Contact Holes: A Challenge for Signal Collection Efficiency and Measurement Algorithms" published in the proceeding of SPIE, vol. 3050, 172–179 (1997) hereinafter the Solecky and Archie technique, it was suggested to analyze the signal that the CD-SEM acquired from an inspected CH in the resist (before etching) in order to determine whether it is open or closed.

Solecky and Archie proposed to attempt and fit a parabola to the waveform by selecting the best three parameters for the formula that define parabola. The quality of the fit, is determined by utilizing a least square fit algorithm and the resulting square of the correlation coefficient (i.e. high $R^2$) is used as a classification criterion. Thus, good fit (i.e. high $R^2$) implies the bottom of the CH is round and therefore the CH is closed, while a bad fit (lower $R^2$) implies that the bottom of the CH is flat and therefore the CH is open. Specifically, they concluded that $R^2=0.08$ differentiates between open and closed CH.

Whilst the proposed approach is basically adequate for classifying CH as open or closed, in suffers from significant shortcomings in that in some real- life scenarios it is not reliable. For a better understanding of the foregoing, attention is directed to FIGS. 1 and 2 showing two examples where the proposed technique according to Solecky and Archie is susceptible to errors.

Figure 1:
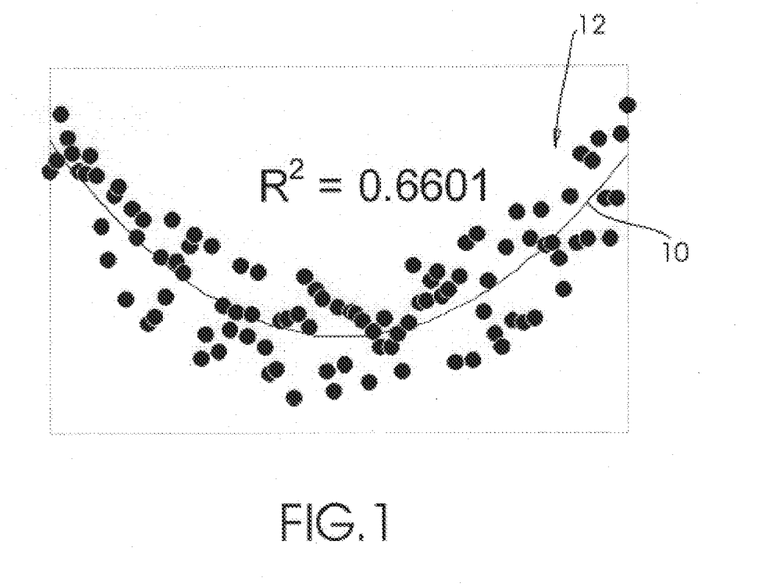
FIG. 1 is a graphic representation of an analysis applied to a synthetic signal imitating a SEM signal that is acquired from an inspected contact hole (CH), according to the prior art.

FIG. 1 illustrates the so called noise problem where due to low contrast to noise ratio (S/N), the distribution of the discrete values of the acquired signal (12) gives rise to a low ($R^2=0.6601$) value. It should be noted that the signal in FIGS. 1 and 2 is not a real signal acquired from inspected CH, but rather a synthetic signal.

Thus, in FIG. 1 the synthetic signal is constructed by taking a signal being of genuine parabola curve (10) and "contaminating" it with noise (12). It would be expected that the Solecky and Archie technique will identify high level of correspondence to parabola (i.e. closed CH), but, regretfully, this was not the case. More specifically, according to the Solecky and Archie criterion the CH under question is open since $R^2$ equals 0.6601 being less than the threshold 0.8. However, since the original signal is of a parabola form, an accurate analysis should have concluded that this particular CH is in fact closed. The net effect is therefore that the bad fit (due to the noisy signal) brings about a faulty indication that the hole under inspection is an open hole.

Figure 2:
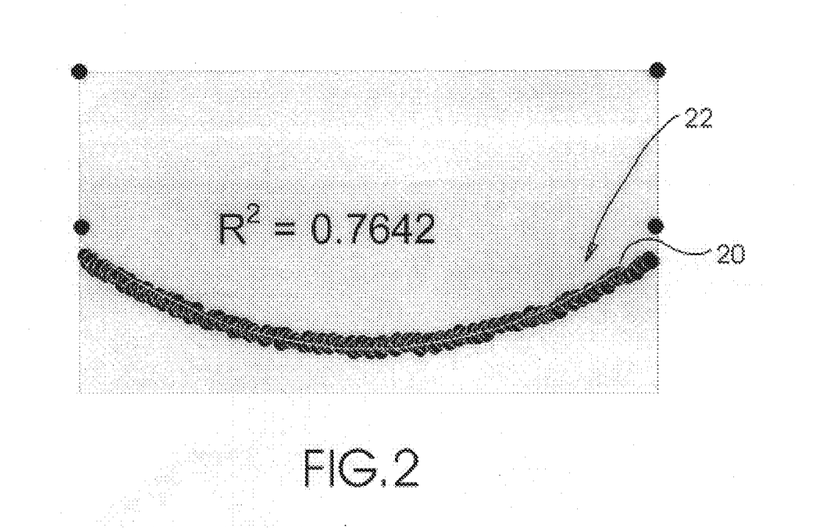
FIG. 2 is a graphic representation of an analysis applied to a different synthetic signal imitating a SEM signal that is acquired from an inspected contact hole (CH), according to the prior art.

Turning now to FIG. 2, there is shown another scenario referred to as the edge problem. Thus, consider an open CH with relatively steep side-walls. Naturally, due to the steepness of the side walls, most of the discrete signal values correspond to the signal that originates form the "bottom" part of the CH and not from the side walls thereof. It has been found that in noiseless signal conditions (i.e. high contrast to noise ratio S/N), the discrete signal values (e.g. 20 in FIG. 2) that originate from the bottom portion fit a parabolic form (e.g. 22 in FIG. 2) in a relatively high degree of accuracy ($R^2=0.7642$) using the thereby erroneous indication that the CH under inspection is closed. As explained above, failing to correctly classify CH could degrade the yield score of the manufactured die series which is highly undesired.

There is accordingly a need in the art to provide for a technique which classifies inspected features (e.g. CH) as open or closed in a reliable manner, and in particular to provide for a technique which substantially copes with the error prone indications of the specified Solecky and Archie technique.

There is yet another need in the art to provide for new technique which enables to grade the profile of an inspected feature according to the profile's quality (constituting a profile's quality grade) which not only enables a coarse classification of the feature as open or closed, but also enables a fine classification for ranking open features according to their quality.

SUMMARY OF THE INVENTION

It should be noted that for convenience of explanation only, reference is made in the following description to contact holes (CH). Those versed in the art will readily appreciate that the invention is by no means bound to CH, but rather applies to any feature that constitutes a going-through aperture in the resist such as trenches (for the pre-etch phase). Features also apply to going-through apertures in a layer of wafer for the post etching phase.

It should be further noted that whilst for convenience of explanation the description refers to a signal acquired by CD-SEM, the invention is by no means bound by this particular embodiment. Accordingly, any metrology tool that is adapted to receive and process signals indicative of the topography of the inspected feature (either in the resist for the pre-etch phase or in the wafer for the post-etch phase), may be utilized in accordance with the invention. A typical, yet not exclusive, example of a metrology tool of the kind specified, is an Atmoic Force Microscope (AFM).

According to a first aspect of the invention, a new technique for a CD-SEM metrology tool has been developed, which allows a quantitative characterization of the contact's profile quality, based on the analysis of the waveform that is acquired from the inside of the CH. An attempt is made to fit a curve from a family of curves (being typically but not necessarily approximated to $X^n$ form) to a SEM signal acquired from an inspected CH, in contrast to the hitherto known technique of Solecky and Archie, where parameters of a parabolic curve of $X^2$ form) are fitted to the so acquired signal and the quality of fit (as exhibited by $R^2$ value) determines whether the inspected CH is open or closed. As explained before, the specified Solecky and Archie technique is error-prone in some real-life scenarios.

According to a second aspect of the invention, a profile quality grade is determined by constraining the fitted curve, in that it must correspond to a signal portion that originates from the side wall or side walls of the inspected hole. The constraining step according to the second aspect is independent of the first aspect. Thus, for example, the constraining may be applied to the technique of the invention (according to the first aspect), or to e.g. the prior art technique of Solecky and Archie.

The analysis according to the invention brings about high quality classification of inspected CH's as open or closed, which as explained above contributes to a better yield score in the FAB.

According to preferred embodiment of the invention, it is possible to grade the quality of the profile of the inspected CH's (applicable, of course, for open CH's). The profile quality grade provides a feed-back tool which enables to re-adjust the operational parameters of the stepper (e.g. focus-exposure matrix and/or other process parameters) so as to produce a new resist having higher quality CH's. As will be explained in greater detail below, the proposed profile quality grade further enables to design in advance (e.g. setting the operational parameters of the stepper) so as to produce resists in which CH's are characterized by high-quality profiles.

Accordingly, the invention provides for a method for determining a profile quality grade of inspected feature in a resist; the feature includes side-walls, the method comprising the steps of:

(a) acquiring by a metrology device at least one signal that originates from the feature;
  (i) analyzing the acquired signal, including: fitting a curve from among a family of curves to at least one acquired signal or portion thereof; said curve is subjected to at least the following constraint: it corresponds to at least one signal portion that originates from at least part of the bottom of the said feature, whereby at least one fitted curve is obtained in respect of said at least one acquired signal;

(b) determining the profile quality grade of said featuure depending upon characteristics of the at least one fitted curve.

In accordance with the second aspect the invention provides for a method for determining a profile quality grade of inspected feature in a resist, the feature includes side walls, the method comprising the steps of:

(a) acquiring by a metrology device at least one signal that originates from the feature;
  (i) analyzing the acquired signal, including fitting a curve to the at least one acquired signal or portion thereof; said curve is subjected to at least the following constraints: it corresponds to at least one signal portion that originates from at least part of the bottom of said feature, and to at least one signal portion that originates from at least a part of the side wall or side walls of said feature; whereby at least one fitted curve is obtained in respect of said at least one acquired signal.

(b) determining the profile quality grade of said feature depending upon characteristics of the at least one fitted curve or the quality of the fitting.

Still further, the invention provides for a method of determining a quality of detection by a CD-SEM, comprising:

(a) measuring a signal level when the CD-SEM is in blank level state; said signal level constituting reference blank level;

(b) analyzing signals originating from a subject when the CD-SEM is in operational state; and (c) checking quality of detection of at least one of said signals by utilizing said reference blank level or derivative thereof, and discarding the analyzed signal whose corresponding signal has insufficient quality of detection.

The invention further provides for a system for determining a profile quality grade of inspected feature, having the elements that correspond to the specified method steps, mutatis mutandis.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

The preferred embodiment will now be described as implemented, utilizing a CD-SEM. However, and as explained, other metrology tools are applicable.

Figure 3:
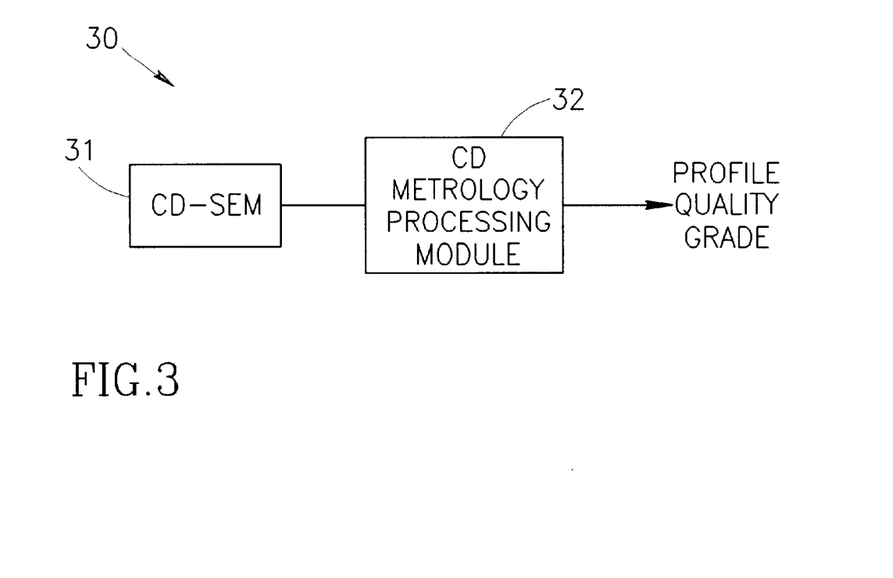
FIG. 3 is a generalized schematic illustration of a system according to the invention.

Attention is first directed to FIG. 3, illustrating a generalized schematic illustration of a system according to the invention. The system (30) generally includes a CD-SEM metrology processing module (32) capable of receiving from a CD-SEM (31) signals that are acquired from within the CH. The operation of the system of FIG. 3 is described with reference also to FIGS. 4 and 5.

It should be noted that the description is confined to the analysis of signals that originate from features of interest. It is accordingly appreciated that various known per se modules in the system, (which are beyond the scope of the present invention and therefore will not be described herein) identify the features of interest which are subjected to the analysis of the invention. Put differently, other areas which are not of interest in the present invention (e.g. the mask portion of the resist), will not be subject to the analysis technique of the invention.

Figure 4:
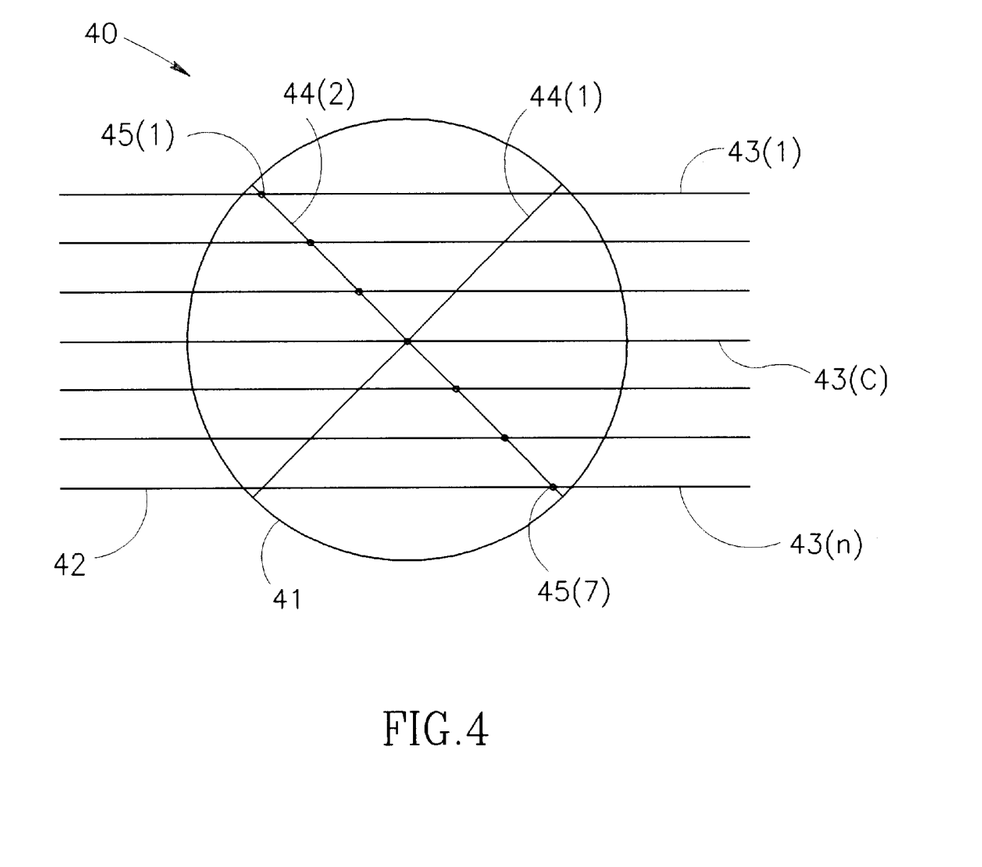
FIG. 4 illustrates a typical CH scan pattern of a CD-SEM.

During operation, the CD-SEM normally scans the inspected region, using an electron beam, according to a scan pattern illustrated for example in FIG. 4 (shown, for clarity, in an enlarged scale). Area (40) in FIG. 4 is confined only to the CH (41) being typically, but not necessarily, of the size of less than a square micrometer—$(\mu m)^2$—and its near surroundings.. The scanning pattern is normally constituted by a succession of parallel scanning lines (43 (1) to 43 (a)), where n is normally determined by the application.

The signal that is acquired from each scanned line by CD-SEM (31) (see step (51)) is delivered to the metrology processing module (32) (obviously after undergoing sampling and possibly other pre-processing steps) for conducting analysis in order to provide for a profile quality grade which, by this particular embodiment, being indicative of whether the inspected CH is open or closed. As will be explained in greater detail below, the specified grade may signify more than simple open/close states.

Whereas according to the prior art an attempt was made to match a parabola to the so acquired signal, in accordance with the invention, an attempt is made to match the so acquired signal or a portion thereof to a family of curves, preferably (but not necessarily) of, or approximated to $X^n$ form (n, not necessarily an integer). An "approximated" $X^n$ should be construed as encompassing, for example, any general power function.

Preferably, the specified curve should be constrained to correspond not only to the bottom part of the CH (or portion thereof), but also to the side all or side walls of the CH. (It is recalled in this connection that the constraining step is not limited to the proposed technique of the invention, and may be applied e.g. to the Solecky and Archie Technique discussed above).

Thus, in accordance with a one embodiment, the following function is fitted to the acquired signal:

$$y(x) = a|x-x_0|^{n+b}$$

Figure 5:
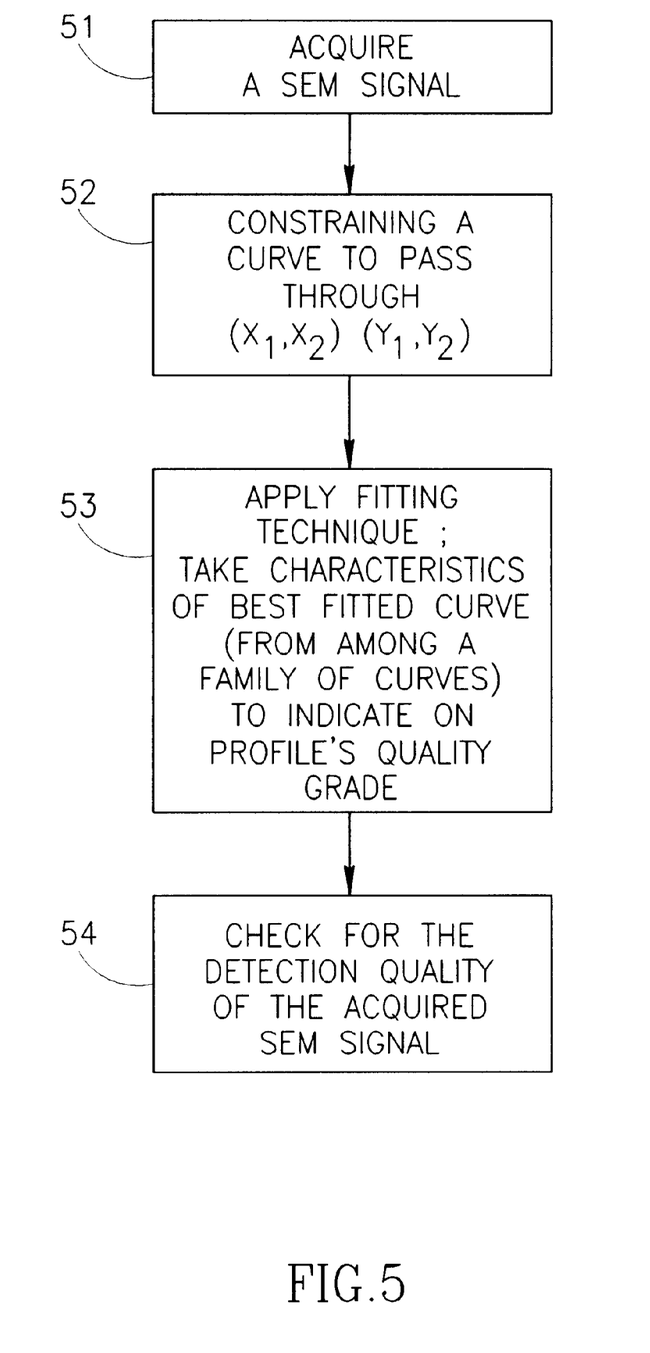
FIG. 5 is a generalized flow chart that illustrates the operation of the system of FIG. 3, according to one embodiment of the invention.

Where:
n is the exponent that characterizes the curve;
a scaling factor allowing for larger/smaller holes;
b stands for the intensity of the central minimum
$x_0$ is the position of the central minimum in the scan direction;

The latter function has, as shown, four unknown parameters n, $x_0$, a, and b. As recalled, according to a preferred embodiment of the invention, the invention, the curve is constrained (step 52) to pass through the side wall of the inspected feature.

By a specific example the latter constraint prescribes that the curve will pass through two opposite coordinates ($x_1$, $y_1$), ($x_2$, $y_2$) in the side wall. The specified coordinates may be selected according to various criteria, e.g. the maximal slope, the edge points, or other, depending upon the particular application.

Now, a and b can be calculated for the following specific cases:

(i) $y=y_1$; $x=x_1$ and (ii) $y=y_2$; $x=x_2$.

Having resolved the values of $a$ and $b$, there results a curve with only two unknown parameters n and $x_0$, as follows:

$$y(x) = (y_2 - y_1)\frac{\left|\frac{x-x_0}{x_1-x_0}\right|^n - 1}{\left|\frac{x_2-x_0}{x_1-x_0}\right|^n - 1} + y_1$$

Where:
n is the exponent that characterizes the curve;
($x_1$, $y_1$), ($x_2$, $y_2$) the side wall coordinates;
$x_0$ is the position of the central minimum in the scan direction;

By this particular embodiment, a variant of the known SIMPLEX optimization technique is utilized for fitting the curve to the acquired signal (step 53). The n value (or derivative thereof, e.g. log n), of the best fitted curve, constitutes the sought feature's profile quality grade. Obviously, the invention is not bound by this particular fitting technique and any known per se fitting technique may be utilized, depending upon the particular application. Moreover, although preferably, the best fitted curve is selected, this is not necessarily the case, and other curve/s (not necessarily having the best fit) may be selected, depending on the particular application.

As specified above, the signal that is analyzed originates form a scanned line that preferably (although no necessarily) passes through the center of the hole (designated $43^{(c)}$ in FIG. 4) (constituting a central scanning line)

Preferably, the analyzing step attempts to find the curve that brings about the best fit. In the latter example, it attempts in finding the n, $x_0$, parameters that ring about the best (or close to best) fit. Having obtained the curve with best fit, the n value thereof serves as the sought feature's profile quality grade.

Figure 6A:
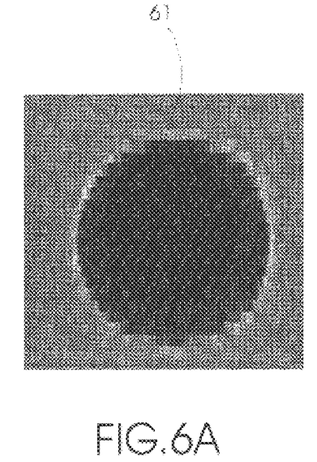
FIG. 6A–B show two images of respective open and closed CH's, that are subject to the analysis technique of the invention.
Figure 6B:
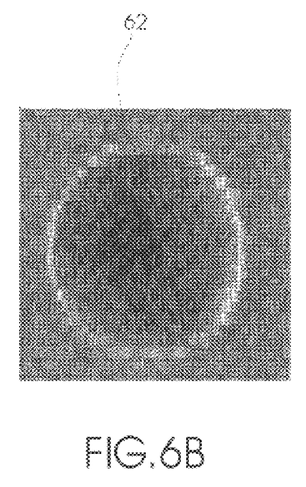

The latter analysis was applied to two exemplary open (61) and closed (62) CH's, respectively (see FIG. 6A–B)

Figure 7:
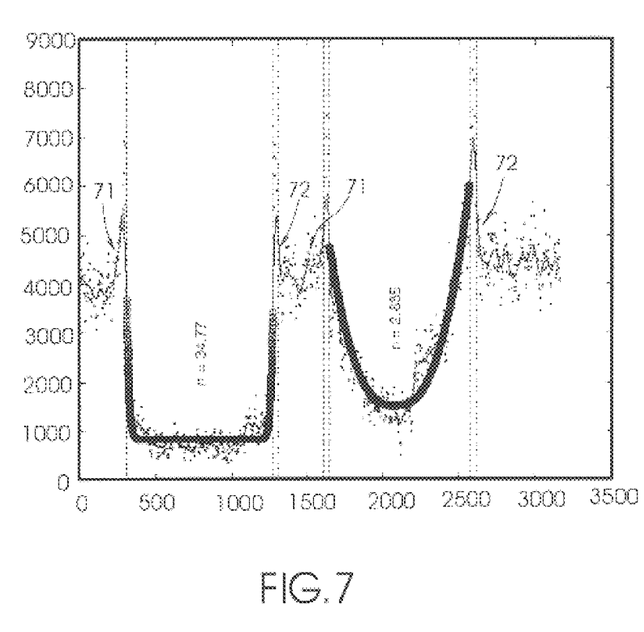
FIG. 7 is a graph representing the resulting curves that match the SEM-signals acquired from the CH's shown in FIG. 6, utilizing an analysis technique, according to one embodiment of the invention.

The resulting fitted curves are illustrated in FIG. 7. As explained above, $(x_1,y_1)$, $(x_2,y_2)$ were constrained to correspond to the maximum slope in the side walls, i.e. the curve must pass through opposite (not necessarily equally high) coordinates which reside on the maximum slope of the signal portion (designated generally as 71 an 72) that originate from the side walls.

As shown in FIG. 7, (with respect to CH 61), the best fit was accomplished for n=34.7, which constitutes a profile quality grade that corresponds to an open CH.

In contrast, and as clearly shown in FIG. 7, the best fit (with respect to CH 62). was accomplished for n=2.6 which constitutes a profile quality grade that corresponds to a closed CH.

Obviously, in order to correlate the so obtained n value to the ultimate classification of open or closed, no should be compared to a reference data, and this will be better clarified in the description below with reference to FIGS. 8 and 9.

Figure 8:
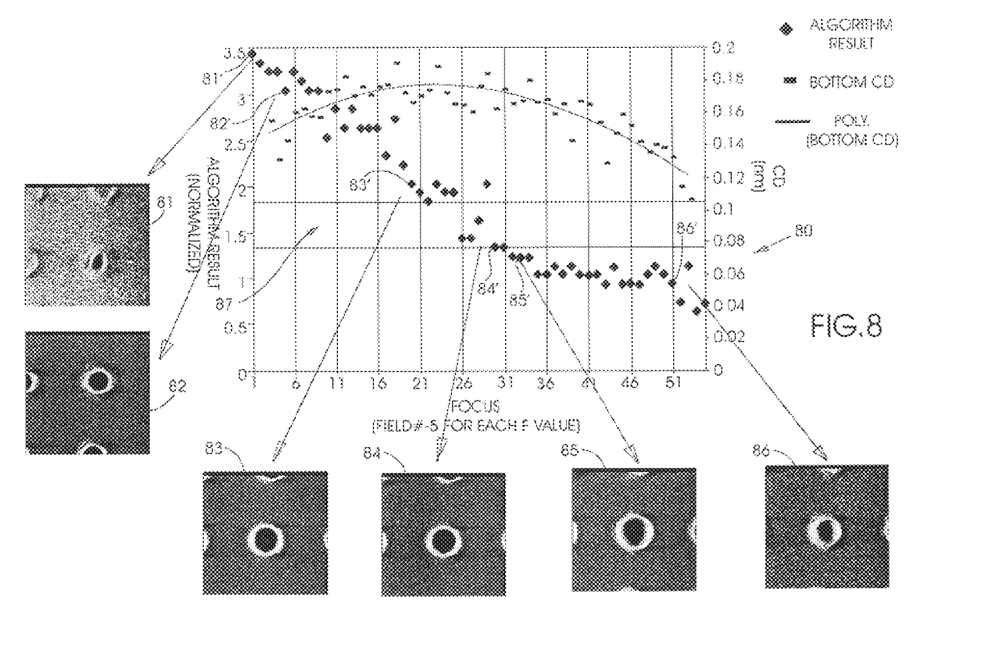
FIG. 8 shows six images representing respective top down views of CH's under inspection, and their corresponding profile quality grades, as obtained in accordance with one embodiment of the invention.

FIG. 8 shows six images representing respective-top down views of CH's under inspection, (81 to 86) and their corresponding profile quality grades (81' to 86'). The profile quality grades are presented in graph (80) where the abscissa indicates the focus of the $CD_{13}SEM$ and the ordinate indicates log n values. Graph (80) further illustrates additional profile quality grades whose corresponding CH's views are not shown. As explained above, according to the invention, the so obtained profile quality grades are not bound to n or log n values. It should be noted that the use of log n rather than n, is done for user convenience in order to reduce the spread and consequently enable him/her to comprehend more easily the so obtained result.

Reverting now to the example of FIG. 8, all those CH's having log n value that clearly exceed 1.5 (i.e. 81 to 83) are classified as open and all those CH's having profile quality grades that drop below 1.5 (i.e. 85 and 86) are classified as closed. CH (84) whose log n value resides in the indecisive zone (87) does not give rise to unequivocal classification. By this particular example, the reference data is taken to be 1.5. The invention is, of course, not bound by this particular reference data.

Figure 9:
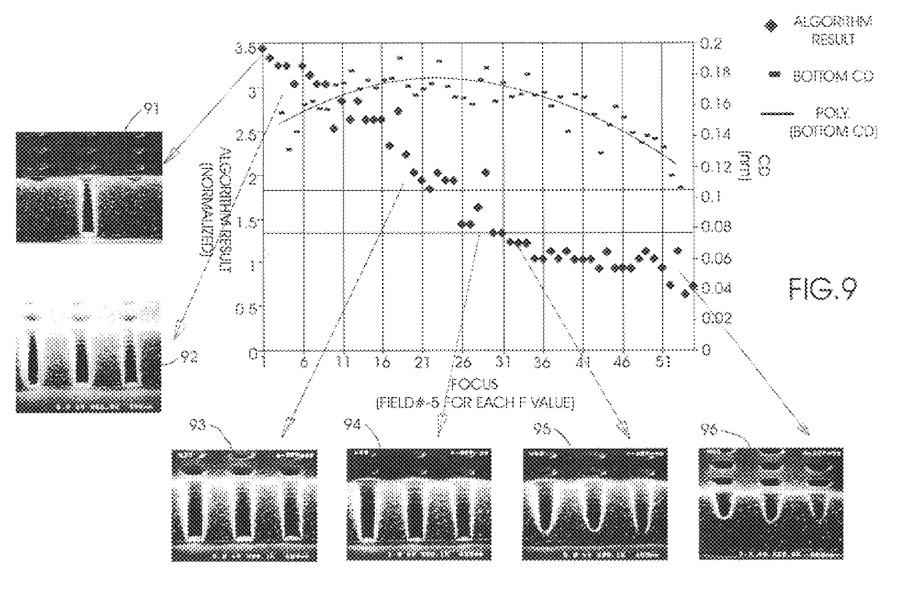
FIG. 9 shows the corresponding cross sectional views of the CH's shown in FIG. 8, and their corresponding profile quality grades, as obtained din accordance with one embodiment of the invention.

FIG. 9 illustrates the actual condition of the inspected CH's (92 to 96). It should be noted that in each image, only the central CH (from among the three CH's that are shown) is of interest. Thus, cross-sectional views (91 to 96) correspond to the top down views (81 to 86). As clearly shown in FIG. 9, all those CH's that were classified as open (81–83) according to their log n value are indeed open (see the going through cross-sections 91 to 93) and likewise, all those CH's that were classified as closed (85–86) according to their log n value are indeed closed (see the cross-sections 95 to 96)

As is well known, the parameters of the stepper (e.g. focus, or other process parameters such as beam current) affect the resulting profile of the features. In particular, modifying said parameters may result in open or closed features.

The proposed technique of the invention provides a powerful took for designing resists according to optimal requirements, e.g. adjusting the focus of the CD-SEM such that the resulting CH's will have associated log n value that falls in the range of say 2–3. Such a design rule assures with high level of confidence that the so produced CH's will be open.

As specified before, the so obtained profile quality grade teaches on more than the basic classification of open/closed feature. Consider, for example, the open CH (91). As clearly shown, the specified CH is characterized by downwardly diverging side-walls (98 and 99) which is believed to constitute a defect despite the fact that the CH under question is open.

CH (91) is associated with a relatively high log n value (3.4). It is accordingly appreciated that by this particular embodiment very high log n score signifies a CH which, although being open, is deemed defective. This provides yet another fine classification which serves as an important quality control tool during the wafer manufacturing process.

The description above focused in analysis of a signal that is acquired from one canning line, say central scanning line $43^{(c)}$ in FIG. 4. The invention is, of course, not bound to this specific embodiment. Thus, for example, other signals that originate from one or more other scanning lines ($43^{(1)}$–$43^{(m)}$) may be subject to analysis in addition or instead the specified central scanning line.

The results of the so obtained analysis in respect of each scanning line are processed to give rise to a final result, e.g. by applying weighted average, weighted majority or possibly other decision techniques, all as required and appropriate, depending upon the particular application. Thus, by way of non limiting example, consider one embodiment of a weighted majority decision algorithm where 5 results are obtained from the analysis of signals acquired from 5 scanning lines, respectively. If two of them indicate on open CH and the rest 3 indicate on closed CH, the result (according to the majority decision criterion) will indicate that the CH under question is closed.

The inherent problem of relying on analysis that arises from actual scanning line is that, all the scanning lines have substantially the same orientation (due to the fact that the electron beam moves always in the same direction). According to the invention it is proposed to (optionally) construct artificial scanning lines from the real scanning lines.

Thus, for example, one or more artificial scanning lines e.g. ($44^{(1)}$ and $44^{(2)}$) are constructed from the signals that originate from the parallel scanning lines ($43^{(1)}$ to $43^{(m)}$. To this end, the artificial scanning line ($44^{(1)}$) can be constructed from the discrete signal values $45^{(1)}$ to $45^{(7)}$ and the values therebetween are interpolated so as to constitute sufficient number of sampled values for accomplishing an analysis of the the acquired signal (as if it had been acquired from a continuous scanning line).

The utilization of results that stem from artificial scanning lines not only enriches the source of information (in addition to the data that is already available from the real scanning lines), but also provide additional perspective, i.e. obtaining information from different directions and naturally deciding about the CH also on the basis of the profile characteristics of the CH, taken from these directions.

The various decision techniques as how to combine the results obtained from different scanning lines apply of course also to information obtained from artificial scanning lines (e.g. weighted average majority and others).

If desired, the ultimate profile quality grade (obtained on the basis of the separate results of distinct scanning lines) may be accompanied with a "level of certainty" rank. Thus, for example, the specified level of certainty rank is higher if all the separate grades (obtained from respective distinct scanning lines) are indicative of, say, open CH, as compared to the level of certainty" rank when i grades indicate that the CH under question is open and j grades (j<i) indicate that the CH is closed. If desired, the spread of the results may be displayed. The latter examples illustrate few out of many possible variants for determining profile and presenting quality grade of the invention.

Finally, in certain real-life scenarios, the analysis technique of the invention is applied to signals even when there is no detection. A "no detection" (or substantially no detection) state may be encountered e.g. in the case of very high aspect ratio CH's measured without $V_{VAR}$ where the incident electron beam is "absorbed" and substantially no secondary electrons are ejected from the CH.

Since, the analysis technique of the invention is insensitive to the nature of the acquired signal it analyzes any signal that is fed thereto even if the latter does not originate from an inspected CH (which is the case in the exemplary no-detection state). The latter scenario is, of course, undesired and accordingly appropriate measures should be taken in order to apply the technique of the invention only to signals that originate (or predominantly originate) from the inspected CH.

To this end, the signal level (hereinafter blank level) is measured when the electron beam is deviated from the water (i.e. it does not incident on the wafer) and is taken to be a reference "blank level" value. Now, any signal whose intensity substantially surpasses the reference level is likely to originates from a CH and therefore should be subject to analysis (see for example the signal of FIG. 7A where the '0' value in the ordinate is taken to be the reference blank level). On the other hand, signals which do not exceed the reference blank level value are discarded. The latter is only one example of checking the detection quality (step 54 in FIG. 5), using the blank level reference value. Thus, according to another non-limiting example, the contrast to noise value is compared to the reference.

The latter approach of discerning between detection and no detection state further improves the correctness of the proposed technique of the invention in terms of obtaining qualitative profile quality grade of inspected features. Those versed in the art will readily appreciate that the utilization of blank level for indicating quality of detection is not bound only to applications of determining profile quality grade of features, and it may be used for other application, all as required and appropriate.

The present invention is by no means bound to the specific examples described above, with reference to FIGS. 3–9, and various alterations and modifications may be applied. Thus, for example, the fitting algorithm and/or the family of curves may be altered (e.g. by adding, modifying or deleting parameters). According to a non limiting modification, a non-symmetric fitting analysis is applied to the acquired signals or portion thereof assuming that by nature the inspected features are asymmetric. Thus, for example, the same curve or (different curve) may be applied to different signal portions that originate from respective parts of the feature, (e.g. first curve is applied to signal originating from first half of the feature, and a second curve is applied to the second half of the feature.) Other variations are, of course, also applicable.

Whereas for convenience of explanation, the invention has been described mainly with reference to resists in a pre-etching phase, it applies mutatis mutandis also to the post etching phase, i.e. to determine the profile quality grade of etched apertures in the overlay layer.

As specified above, the constraining step according to the second aspect of the invention may be applied not only to the technique according to the first aspect of the invention. Thus, for example, the fitting parabola curve (e.g. the one shown in FIG. 2), is constrained to pass through the side walls of the CH, thereby improving the likelihood that the CH will be correctly classified as open. The possible improved result (which, as recalled, was not the case when the Solecky and Archie technique was utilized "as is"), would be accomplished since the edges are also taken into account in the analysis due to the specified constraining step.

By another modified embodiment, the fitting of a curve is not necessarily performed for each respective acquired signal (e.g. a curve is fitted to the signal originating from scanning line 43(1), another curve is fitted to the signal originating from scanning line 43(2)), etc. Accordingly, by this modified embodiment, two or more signals (or portion thereof) are subject to fitting by one curve. Thus, for example, the signals that originate from scanning lines 43(1) and 43(2) will be subject to fitting by one curve.

Alphabetical letters and Roman numerals are designated in the claims for convenience only, and do not necessarily imply a given order of method steps.

The present invention has been described with a certain degree of particularity, but various alterations and modifications may be carried out without departing from the spirit and the scope of the following claims:

What is claimed is:

1. A method for determining a profile quality grade of an inspected feature in a resist, wherein the feature includes side-walls, the method comprising the steps of:
   (a) acquiring at least one signal from a metrology device, said at least one signal originating from the feature;
      (i) analyzing the acquired signal, comprising the steps of:
         fitting a curve from among a family of curves to the at least one acquired signal or portion thereof, said curve being subjected to at least a constraint that said curve correspond to at least one signal portion that originates from at least part of a bottom of the feature,
      whereby at least one fitted curve is matched with said at least one acquired signal; and
   (b) determining the profile quality grade of said feature depending upon characteristics of the at least one fitted curve.

2. The method of claim 1, wherein said step (a) includes acquiring at least one signal, each signal originating from a distinct scanning line in said feature; wherein for each signal, step (a) further comprises:
   (i) analyzing the acquired at least one signal, including fitting a curve from among a family of curves to the at least one acquired signal or portion thereof; said curve being subjected to at least a constraint that said curve correspond to at least one signal portion that originates from at least part of the bottom of said feature; said step (b) further comprising:
      (i) determining at least one profile grade in respect of said at least one fitted curve and combining said profile grades to obtain said profile quality grade of the inspected feature.

3. The method of claim 2, wherein said step (b)(i) includes: applying a weighted average technique to said profile grades so as to obtain said profile quality grade of the inspected feature.

4. The method of claim 2, wherein said step (b)(i) includes: applying a weighted majority technique to said profile grades so as to obtain said profile quality grade of the inspected feature.

5. The method of claim 2 wherein the family of curves in step (a)(i) are of a general power function form, and said fitted curve has substantially the best fit characteristics compared to the acquired signal from among the rest of the curves in said family of curves; and said step (b) further comprises:
determining said profile quality grade based on the characteristic of the at least one fitted curve.

6. The method of claim 2 wherein said step (a)(i) includes: fitting to the acquired signal or portion thereof a curve from among a family of curves that comply with the following algorithmic expression:

$$y(x) = (y_2 - y_1) \frac{\left|\frac{x - x_0}{x_1 - x_0}\right|^n - 1}{\left|\frac{x_2 - x_0}{x_1 - x_0}\right|^n - 1} + y_1$$

Where:
n is the exponent that characterizes the curve;
$(x_1, y_1)$, $(x_2, y_2)$ the side all coordinates;
$X_0$ is the position of the central minimum in the scan direction.

7. The method of claim 2, further comprising the step of: constructing at least one artificial scanning line from at least two scan lines; said step (a) further includes: acquiring at least one signal originating from respective at least one artificial scanning line.

8. The method of claim 7, wherein said artificial scanning line is constructed by taking real scanning line values and interpolating values between neighboring scanning line values so as to give rise to sufficient artificial scanning line values.

9. The method of claim 2, wherein said step (b) includes: determining the profile quality grade of said feature depending upon characteristics of the at least one fitted curve; the profile quality grade of said feature signifies whether said feature is open or closed.

10. The method of claim 7, wherein said step (b) includes: determining the profile quality grade of said feature depending upon characteristics of the at least one fitted curve; the profile quality grade of said feature signifies whether said feature is open or closed.

11. The method of claim 7, wherein said feature is selected from the group that includes: contact hole and trench.

12. The method of claim 7, wherein said metrology device being a CD-SEM.

13. The method of claim 7, wherein said metrology device being an AFM.

14. The method of claim 2, wherein said feature is selected from the group that includes: contact hole and trench.

15. The method of claim 2, wherein said curve, stipulated in said step (a)(i) is subject to the following additional constraint:

the curve corresponds also to at least one signal portion that originates from at least a part of the side wall or side walls of said feature.

16. The method of claim 2, wherein said metrology device being a CD-SEM.

17. The method of claim 2, wherein said metrology device being an AFM.

18. The method of claim 1, wherein the family of curves in step (a)(i) are of a general power function form, and said fitted curve has substantially the best fit characteristics compared to the acquired signal from along the rest of the curves in the family of curves; and said step (b) further comprises:
determining said profile quality grade based on the characteristic of the at least one fitted curve.

19. The method of claim 18, wherein said step (a)(i) includes: fitting to the acquired signal or portion thereof a curve from among a family of curves that comply with the following algorithmic expression:

$$y(x) = (y_2 - y_1) \frac{\left|\frac{x - x_0}{x_1 - x_0}\right|^n - 1}{\left|\frac{x_2 - x_0}{x_1 - x_0}\right|^n - 1} + y_1$$

Where:
n is the exponent that characterizes the curve;
$(x_1, y_1)$, $(x_2, y_2)$ the side wall coordinates;
$X_0$ is the position of the central minimum in the scan direction.

20. The method of claim 19 further comprising the step of: constructing at least one artificial scanning line from at least two of said scan lines; said step (a) further includes: acquiring at least one signal originating from respective at least one artificial scanning line.

21. The method of claim 20, wherein said artificial scanning line is constructed by taking real scanning line values and interpolating values between neighboring scanning line values so as to give rise to sufficient artificial scanning line values.

22. The method of claim 17, wherein said step (b) includes: determining the profile quality grade of said feature depending upon characteristics of the at least one fitted curve; the profile quality grade of said feature signified whether said feature is open or closed.

23. The method of claim 19, wherein said feature is selected from the group that includes: contact hole and trench.

24. The method of claim 19, wherein said metrology device being a CD-SEM.

25. The method of claim 19, wherein said metrology device being an AFM.

26. The method of claim 18, further comprising step of: constructing at least one artificial scanning line from at least two of said scan lines; said step (a) further includes: acquiring at least one signal originating from respective at least one artificial scanning line.

27. The method of claim 26, wherein said artificial scanning line is constructed by taking real scanning line values and interpolating values between neighboring scanning line values so as to give rise to sufficient artificial scanning line values.

28. The method of claim 18, wherein said step (b) includes: determining the profile quality grade of said feature depending upon characteristics of the at least one fitted curve; the profile quality grade of said feature signifies whether said feature is open or closed.

29. The method of claim 18, wherein said feature is selected from the group that includes: contact hole and trench.

30. The method of claim 18, wherein said metrology device being a CD-SEM.

31. The method of claim 18, wherein said metrology device being an AFM.

32. The method of claim 1, wherein said step (b) includes: determining the profile quality grade of said feature depending upon characteristics of the at least one fitted curve; the profile quality grade of said feature signifies whether said feature is open or closed.

33. The method of claim 32, wherein said feature is selected from the group that includes: contact hole and trench.

34. The method of claim 32, wherein said metrology device being a CD-SEM.

35. The method of claim 32, wherein said metrology device being an AFM.

36. The method of claim 1, wherein said feature is selected from the group that includes: contact hole and trench.

37. The method of claim 36, wherein said metrology device being a CD-SEM.

38. The method of claim 36, wherein said metrology device being an AFM.

39. The method of claim 1, wherein said curve, stipulated in said step (a)(i) is subject to the following additional constraint:

the curve corresponds also to at least one signal portion that originates from at least a part of the side wall or side walls of said feature.

40. The method of claim 39, wherein the family of curves in step (a)(i) are of a general power function form, and said fitted curve has substantially the best fit characteristics compared to the acquired signal from among the rest of the curves in said family of curves; and said step (b) further comprises:

determining said profile quality grade based on the characteristic of the at least one fitted curve.

41. The method of claim 39, wherein said step (a)(i) includes: fitting to the acquired signal or portion thereof a curve from among a family of curves that comply with the following algorithmic expression;

$$y(x) = (y_2 - y_1) \frac{\left|\frac{x-x_0}{x_1-x_0}\right|^n - 1}{\left|\frac{x_2-x_0}{x_1-x_0}\right|^n - 1} + y_1$$

Where:

n is the exponent that characterizes the curve;

$(x_1, y_1)$, $(x_2, y_2)$ the side wall coordinates;

$x_0$ is the position of the central minimum in the scan direction.

42. The method of claim 39, further comprising the step of: constructing at least one artificial scanning line from at least two of said scan lines; said step (a) further includes: acquiring at least one signal originating from respective at least one artificial scanning line.

43. The method of claim 39, wherein said step (b) includes: determining the profile quality grade of said feature depending upon characteristics of the at least one fitted curve; the profile quality grade of said feature signifies whether said feature is open or closed.

44. The method of claim 39, wherein said feature is selected from the group that includes: contact hole and trench.

45. The method of claim 39, wherein said metrology device being a CD-SEM.

46. The method of claim 36, wherein said metrology device being an AFM.

47. The method of claim 1, wherein said metrology device being a CD-SEM.

48. The method of claim 1, wherein said metrology device being an AFM.

49. A method for determining a profile quality grade of an inspected feature in a layer of a wafer, wherein the feature includes side-walls, the method comprising the steps of:

(a) acquiring at least one signal from a metrology device, said at least one signal originating from the feature;
(i) analyzing the acquired signal, comprising the steps of: fitting a curve from among a family of curves of a specified form to the at least one acquired signal or portion thereof, said curve being subjected to at least a constraint that the curve correspond to at least one signal portion that originates from at least part of a bottom of the feature,
whereby at least one fitted curve is matched with said at least one acquired signal; and (b) determining the profile quality grade of said feature depending upon characteristics of the at least one fitted curve.

50. A method for determining a profile quality grade of inspected feature in a resist, the feature includes side walls, the method comprising the steps of:

(a) acquiring at least one signal from a metrology device, said at least one signal originating from the feature;
(i) analyzing the acquired signal, comprising the steps of fitting a curve to the at least one acquired signal or portion thereof; said curve being subjected to at least constraints that correspond to at least one signal portion that originates from at least part of a bottom said feature, and to at least one signal portion that originates from at least a part of the side wall or side walls of said feature;
whereby at least one fitted curve is matched with said at least one acquired signal; and (b) determining the profile quality grade of said feature depending upon characteristics of the at least one fitted curve or the quality of the fitting.

51. The method of claim 50, wherein said part of side walls stipulated in step a(i), is constituted by the coordinated $(x_1,y_1)$ and $(x_2,y_2)$ in opposite side walls of said feature.

52. The method of claim 50, wherein the fitting stipulated in said step (i) is realized by the Solecky and Archie technique and wherein said step (b) includes: determining the profile quality grade of said feature depending upon the quality of the fitting as constituted by the square of correlation coefficient $R^2$.

53. A method of determining a quality of detection by a CD-SEM comprising the steps of:

(a) measuring a signal level when an electron beam of the CD-SEM is deviated from a subject and defining the signal level as a reference blank level;

(b) analyzing signals originating from a subject when the CD-SEM is in operational state with the electron beam incident on the subject; and (c) comparing the quality of detection of at least one of said signals with said reference blank level or a derivative thereof, and discarding the analyzed signal whose corresponding signal does not exceed the measured reference blank signal as having insufficient quality of detection, wherein said analyzing step stipulated in step (b) is performed by fitting a curve from among a family of curves to the at least one acquired signal or portion thereof, said curve being subjected to at least a constraint that said curve correspond to at least one signal portion that originates from at least part of a bottom of the feature, whereby at least one fitted curve is matched with said at least one acquired signal.

* * * * *